US00PP20256P3

(12) United States Plant Patent
Noodelijk

(10) Patent No.: US PP20,256 P3
(45) Date of Patent: Sep. 1, 2009

(54) *CHRYSANTHEMUM* PLANT NAMED 'SUNNO YELLOW'

(50) Latin Name: *Chrysanthemum morifolium*
Varietal Denomination: Sunno Yellow

(76) Inventor: Robert Noodelijk, Vrouwgeestweg 26, Woubrugge (NL), 2481 KN ( * ) Notice: Subject to any disclaimer, the term of this patent is extended or adjusted under 35 U.S.C. 154(b) by 48 days.

(21) Appl. No.: 12/002,415

(22) Filed: Dec. 17, 2007

(65) Prior Publication Data

US 2009/0158483 P1 Jun. 18, 2009

(51) Int. Cl.
*A01H 5/00* (2006.01)

(52) U.S. Cl. ..... Plt./295

(58) Field of Classification Search ..... Plt./295, Plt./286

See application file for complete search history.

*Primary Examiner*—Susan B McCormick Ewoldt

(74) *Attorney, Agent, or Firm*—Jondle & Associates, P.C.

(57) ABSTRACT

A *chrysanthemum* plant named 'Sunno Yellow' characterized by small-sized blooms with yellow ray florets and prolific branching, a natural season flowering date of September 14, a blooming period of 6 weeks, a rounded plant habit and a spreading growth habit, is disclosed.

1 Drawing Sheet

Genus: *Chrysanthemum morifolium.*
Variety denomination: 'Sunno Yellow'.

BACKGROUND OF THE INVENTION

'Sunno Yellow' is a product of a breeding and selection program for outdoor pot mums (garden mums) which had the objective of creating new *chrysanthemum* cultivars with a daisy-type flower, a natural season flowering date around September 25 and a blooming period of 6 weeks. The new plant of the present invention comprises a new and distinct cultivar of *chrysanthemum* plant.

'Sunno Yellow' is a seedling resulting from the open pollination among groups of un-named, unknown, unpatented *chrysanthemum* cultivars maintained under the control of the inventor for breeding purposes. The new and distinct cultivar was discovered and selected as one flowering plant by Rob Noodelijk on a cultivated field in Woubrugge, The Netherlands in September 2005. The plant has been asexually reproduced by cuttings in greenhouses at Woubrugge, The Netherlands over a two year period. The new cultivar has been found to retain its distinctive characteristics through successive propagations.

SUMMARY OF THE INVENTION

The following are the most outstanding and distinguishing characteristics of the new cultivar when grown under normal horticultural practices in Woubrugge, The Netherlands.

1. Small yellow flowers with yellow centers:
2. A rounded plant habit;
3. A blooming period of 6 weeks and a blooming date of September 25;
4. A spreading growth habit; and
5. Prolific branching.

DESCRIPTION OF THE PHOTOGRAPHS

The present invention of a new and distinct variety of *chrysanthemum* is shown in the accompanying photographs, the colors being as nearly true as possible with color photographs of this type.

DESCRIPTION OF THE INVENTION

Figure 1:
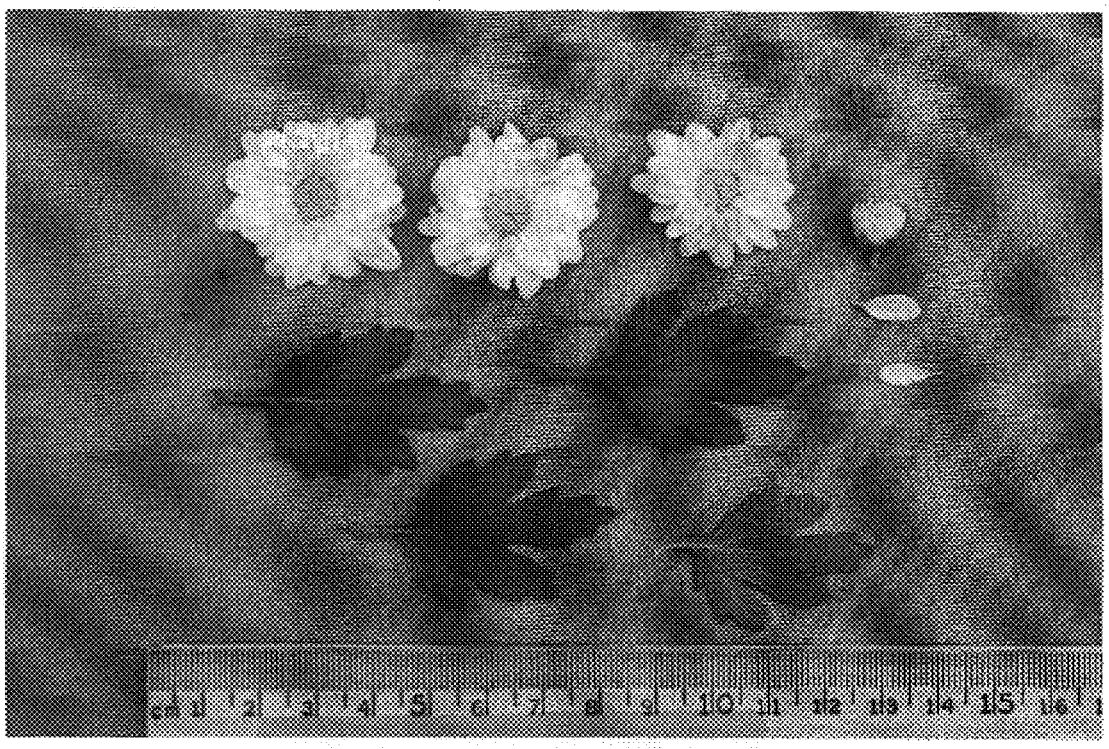
FIG. 1 shows a close-up of the bud, florets, leaves and individual flowers.
Figure 2:
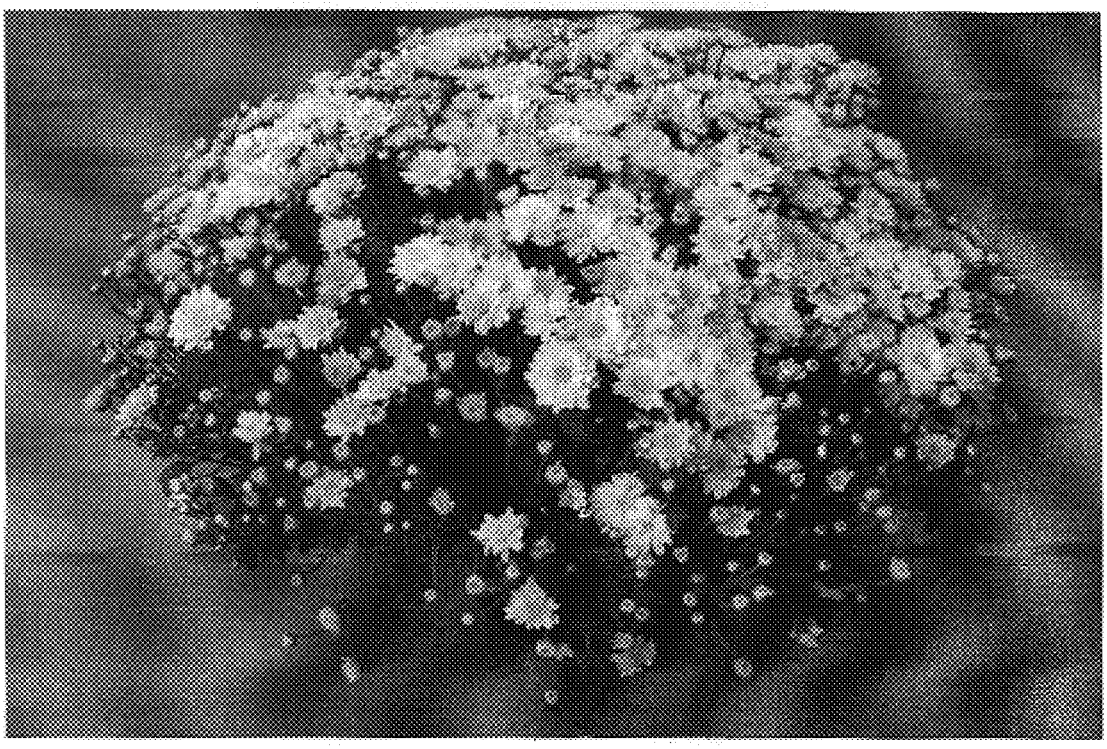
FIG. 2 shows a plant of the cultivar in full bloom.

This new variety of *chrysanthemum* is of the botanical classification *Chrysanthemum morifolium.* The observations and measurements were gathered from plants grown outdoors in Woubrugge, The Netherlands under natural day length and temperature and planted in week 22 in 2005 and 2006. The natural blooming date of this crop was September 25. The average height of the plants was 35 cm. No growth retardants were used. No tests were done on disease or insect resistance or susceptibility. No tests were done on cold or drought tolerance. This new variety produces small-sized blooms with yellow ray florets and yellow centers blooming for a period of 6 weeks.

The following is a description of the plant and characteristics that distinguish 'Sunno Yellow' as a new and distinct variety. The color designations are taken from the plant itself. Accordingly, any discrepancies between the color designations and the colors depicted in the photographs are due to photographic tolerances. The color chart used in this description is The Royal Horticultural Society Colour Chart, edition 1995.

BOTANICAL DESCRIPTION OF 'SUNNO YELLOW'

Plant:

*Shape.*—Rounded.

*Growth habit.*—Spreading.

*Growth rate.*—Slow.
*Height.*—32 cm to 36 cm.
*Width.*—38 cm 40 cm.

Branches:
*Stem.*—Color: RHS 137C (green). Strength: Flexible. Brittleness: Absent. Anthocyanin Coloration: Absent.
*Length of lateral branch* (*from top to bottom*).—10 cm to 15 cm.
*Lateral branch color.*—RHS 137C (green).
*Lateral branch attachment.*—Petiolate.
*Branching* (*average number of lateral branches*).—Very prolific with 12 breaks after pinching.

Leaves:
*Color.*—Upper surface: RHS 147B (yellow-green). Lower surface: RH 147B (yellow-green).
*Size.*—General: Small. Length: 2.9 cm to 3.2 cm. Width: 2.3 cm to 2.5 cm.
*Quantity* (*number per lateral branch*).—6 to 7.
*Shape.*—Ovate.
*Apex.*—Acute.
*Base.*—Asymmetric.
*Margin.*—Serrate.
*Texture.*—Upper surface: Glabrous. Lower surface: Pubescent.
*Venation arrangement.*—Palmate.
*Shape of base of sinus between lateral lobes.*—Acute.
*Margin of sinus between lateral lobes.*—Mostly diverging sometimes converging.

Bud:
*Size.*—General: Small. Cross-section: 0.8 cm. Height: 0.6 cm.
*Outside color.*—RHS 6A (yellow).
*Involucral bracts.*—2 rows, length 0.7 cm, width 0.3 cm.
*Involucral bracts among disc-florets.*—Absent.
*Involucral bracts color.*—RHS 138A (green).

Bloom:
*Type.*—Daisy.
*Size.*—General: Small. Fully expanded: 2.8 cm to 3.2 cm.
*Number of blooms per branch.*—Approximately 9 to 10 blooms per branch.
*Performance on the plant* (*blooming period*).—6 weeks.
*Fragrance.*—Typical *chrysanthemum,* slight.
*Tonality from distance.*—A very rich flowering garden mum with small yellow flowers and a yellow flower disc.
*Discoloration to color.*—None.
*Peduncle.*—Length: 6 cm to 7 cm. Color: RHS 137C (green).
*Natural season blooming date.*—25 September.

Ray florets:
*Texture.*—Both the upper and lower surfaces are smooth.
*Number.*—80 to 100.
*Cross-section.*—Flat to concave.
*Longitudinal axis of majority.*—Straight.
*Length of corolla tube.*—0.3 cm.
*Apex.*—Rounded.
*Margin.*—Entire.
*Length.*—0.7 cm to 1.0 cm.
*Width.*—0.3 cm.
*Ratio length/width.*—Medium.
*Color.*—Upper surface of the outer ray-florets: RHS 5B (yellow). Lower surface of the ray-florets: RHS 5B (yellow).

Disc florets:
*Disc diameter.*—1.0 cm.
*Distribution of disc florets.*—Numerous, clearly visible at all stages of flowering.
*Shape.*—Tubular.
*Color.*—RHS 12A (yellow).
*Receptacle shape.*—Conical flat.
*Color of center of the flower* (*disc-florets*).—Immature: RHS 12A (yellow). Mature: RHS 12A (yellow).

Reproductive organs:
*Stamen* (*present in disc florets only*).—Thin, 0.2 cm to 0.3 cm.
*Stamen color.*—RHS 144A (yellow-green).
*Pollen.*—Appears in a very late stage.
*Pollen color.*—RHS 12A (yellow).
*Styles.*—Thin.
*Style color.*—RHS 144A (yellow-green).
*Style length.*—0.3 cm to 0.4 cm.
*Stigma color.*—RHS 144A (yellow-green).
*Stigma width.*—0.1 cm.
*Ovaries.*—Enclosed in calyx.

Fruit/seed set: Seeds are produced in small quantities; ovate RHS 199A (grey-brown) and 0.15 cm in length.

COMPARISON WITH COMMERCIAL CULTIVARS

'Sunno Yellow' differs from the commercial cultivar 'Sunny Yocamille' (U.S. Plant Pat. No. 15,347) in that 'Sunno Yellow' flowers later (September 25) than 'Sunny Yocamille' (September 19). Additionally, 'Sunno Yellow' has stronger vigor and darker yellow flowers than 'Sunny Yocamille'.

I claim:

1. A new and distinct variety of *chrysanthemum* plant as described and illustrated.

* * * * *